United States Patent [19]
Jeschke et al.

[11] Patent Number: 5,985,904
[45] Date of Patent: *Nov. 16, 1999

[54] 1,2,4-OXADIAZOLE DERIVATIVES AND THEIR USE AS PARASITICIDES FOR ANIMALS

[75] Inventors: Peter Jeschke, Leverkusen; Ulrike Wachendorff-Neumann, Neuwied; Christoph Erdelen, Leichlingen; Andreas Turberg, Erkrath; Norbert Mencke, Leverkusen, all of Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/669,482
[22] PCT Filed: Jan. 4, 1995
[86] PCT No.: PCT/EP95/00024
  § 371 Date: Jul. 11, 1996
  § 102(e) Date: Jul. 11, 1996
[87] PCT Pub. No.: WO95/19353
  PCT Pub. Date: Jul. 20, 1995

[30] Foreign Application Priority Data

Jan. 17, 1994 [DE] Germany ............... 44 01 108

[51] Int. Cl.⁶ .................. A61K 31/41; C07D 271/06
[52] U.S. Cl. ............. 514/364; 514/340; 546/269.4; 548/131
[58] Field of Search ............... 548/131; 514/364, 514/340; 546/269.4

[56] References Cited

U.S. PATENT DOCUMENTS

| | | | |
|---|---|---|---|
| 5,037,467 | 8/1991 | Cho et al. | 71/87 |
| 5,428,047 | 6/1995 | Jeschke et al. | 514/364 |

FOREIGN PATENT DOCUMENTS

| | | |
|---|---|---|
| 7529 | 2/1980 | European Pat. Off. . |
| 0 036 711 | 9/1981 | European Pat. Off. . |
| 273534 | 7/1988 | European Pat. Off. . |
| 0 590 415 | 4/1994 | European Pat. Off. . |

*Primary Examiner*—Laura L. Stockton
*Attorney, Agent, or Firm*—Sprung Kramer Schaefer & Briscoe

[57] ABSTRACT

The invention relates to 1,2,4-oxadiazole derivatives of the formula (I)

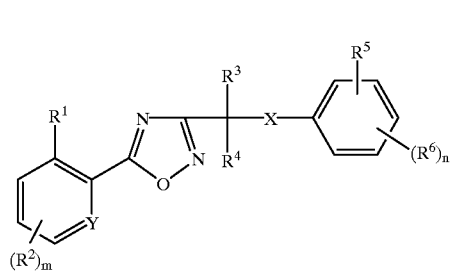

in which
  $R^1$, $R^2$, $R^3$, $R^4$, $R^5$, $R^6$, X, Y, m and n have the meanings given in the description,
to a plurality of processes for their preparation, and to their use as pesticides.

10 Claims, No Drawings

1,2,4-OXADIAZOLE DERIVATIVES AND THEIR USE AS PARASITICIDES FOR ANIMALS

This application is a 371 of PCT/EP95/00024 filed Jan. 4, 1995.

The invention relates to new 1,2,4-oxadiazole derivatives, to a plurality of processes for their preparation, and to their use for combating animal pests.

A range of substituted 1,2,4-oxadiazole derivatives have already been disclosed as compounds for use in the control of parasitic protozoans (cf. EP 7 529, EP 8 356), as analgesics (GB 1 198 726) or as herbicides (JP 57 175 177) (cf. also the earlier, but not published, Patent Application DE-P 42 32 418 by the Applicant Company).

Furthermore, the preparation of substituted 1,2,4-oxadiazole derivatives, such as, for example, 5-(4-chlorophenyl)-3-[2-(2,4-dichlorophenyl)ethyl]-1,2,4-oxadiazole and 5-(2,4-dichlorophenyl)-3-[2-(2,4-dichlorophenyl)ethyl]-1,2,4-oxadiazole is described (J. Heterocycl. Chem., 15 (8), 1373–8, 1978). However, its use for combating animal pests has not been disclosed.

New 1,2,4-oxadiazole derivatives have now been found, of the formula (I)

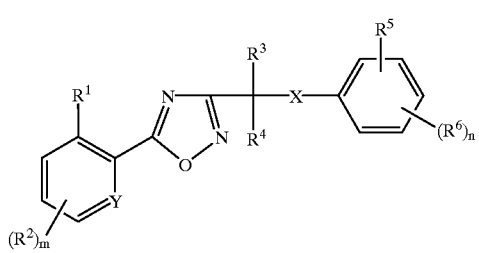

in which
R$^1$ represents halogen, alkyl or alkoxy,
R$^2$ represents hydrogen, halogen, halogenoalkyl or halogenoalkoxy,
R$^3$ represents hydrogen or alkyl,
R$^4$ represents hydrogen or alkyl,
R$^5$ represents halogen, trialkylsilylalkyl, trialkylsilylalkoxy;
or a group —A$_k$—R$^7$
in which
A represents oxygen, sulfur, SO, SO$_2$, alkylene, alkyleneoxy, alkylenethio, oxyalkylene, oxyalkyleneoxy, alkyleneoxyalkylene, alkenediyl or alkindiyl,
k represents a number 0 or 1,
R$^7$ represents alkyl, halogenoalkyl, alkenyl, halogenoalkenyl, alkinyl, halogenoalkinyl, optionally substituted cycloalkyl, optionally substituted phenyl or optionally substituted pyridyl, or
R$^5$ represents optionally substituted cycloalkyl, it being possible for one or two CH$_2$ groups which are not bonded directly to each other to be replaced by oxygen and/or sulfur,
R$^6$ represents hydrogen, halogen, alkyl, halogenoalkyl, alkoxy or halogenoalkoxy,
m represents a number 1, 2 or 3,
n represents a number 1, 2 or 3,
x represents O, S, SO, SO$_2$, CH$_2$ or a group N—R$^8$ in which
R$^8$ represents hydrogen or alkyl and
Y represents a nitrogen atom or the group C—R$^9$
in which
R$^9$ represents hydrogen, halogen or alkyl;
with the exception of the compounds:
5-(4-chlorophenyl)-3-[2-(2,4-dichlorophenyl)ethyl]-1,2,4-oxadiazole and 5-(2,4-dichlorophenyl)-3-[2-(2,4-dichlorophenyl)ethyl]-1,2,4-oxadiazole (cf. J. Heterocycl. Chem. 15 (8), 1373–8, 1978) and 3-(4-tert-butylphenoxymethyl)- 5-(2,6-difluorophenyl)-1,2,4-oxadiazole (cf. DE-P 42 32 418).

Depending on the nature of the substituents, the compounds of the formula (I) can exist in the form of geometric and/or optical isomers or variously composed isomer mixtures. The invention relates to the pure isomers as well as to the isomer mixtures.

Furthermore, it has been found that the new 1,2,4-oxadiazole derivatives of the formula (I) are obtained when a) compounds of the formula (II)

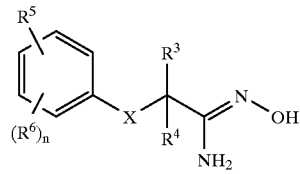

in which
n, X, R$^3$, R$^4$, R$^5$ and R$^6$ have the abovementioned meanings
are reacted with carboxylic acid derivatives of the formula (III), (IV) or (V)

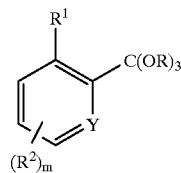

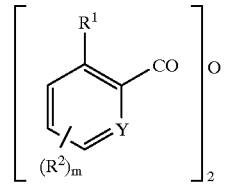

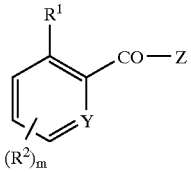

in which
R$^1$, R$^2$, m and Y have the abovementioned meanings,
R represents alkyl, preferably methyl or ethyl, and
Z represents a suitable leaving group such as, for example, halogen, or b) compounds of the formula (VI)

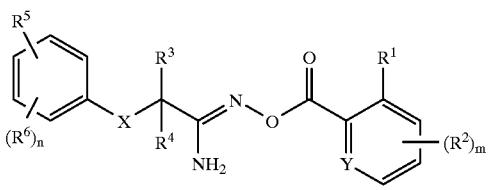

in which
X, Y, $R^1$, $R^2$, $R^3$, $R^4$, $R^5$, $R^6$, m and n have the abovementioned meanings are subjected to a cyclization reaction, if appropriate in the presence of a diluent and if appropriate in the presence of a reaction auxiliary, or c) compounds of the formula (VII)

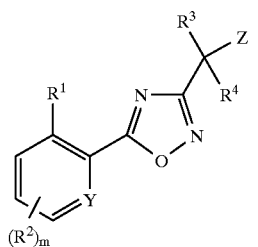

in which
$R^1$, $R^2$, $R^3$, $R^4$, Y and m have the abovementioned meanings and
Z represents a suitable leaving group are reacted with compounds of the formula (VIII)

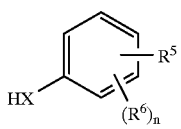

in which
X, $R^5$, $R^6$ and n have the abovementioned meanings, in the presence of a diluent and, if appropriate, in the presence of a reaction auxiliary.

Furthermore, it has been found that the new 1,2,4-oxadiazole derivatives of the formula (I) are highly suitable for combating animal pests. In particular, they are distinguished by a powerful activity against arthropods and nematodes.

Surprisingly, the new 1,2,4-oxadiazole derivatives of the formula (I) according to the invention show considerably better activity against animal pests than the prior art compounds which have a similar constitution.

Formula (I) provides a general definition of the compounds according to the invention.

Preferred substituents or ranges of the radicals mentioned in the formulae hereinabove and hereinbelow are illustrated in the following text:

$R^1$ preferably represents fluorine, chlorine, bromine, $C_1$–$C_6$-alkyl or $C_1$–$C_6$-alkoxy.

$R^2$ preferably represents hydrogen, fluorine, chlorine, bromine, $C_1$14 $C_6$-halogenoalkyl or $C_1$–$C_6$-halogenoalkoxy.

$R^3$ preferably represents hydrogen or $C_1$–$C_4$-alkyl.

$R^4$ preferably represents hydrogen or $C_1$–$C_4$-alkyl.

$R^5$ preferably represents fluorine, chlorine, bromine, tri-($C_1$–$C_8$-)-alkyl-silyl-($C_1$–$C_6$-)-alkyl or tri-($C_1$–$C_8$-)-alkyl-silyl-($C_1$–$C_6$-)-alkoxy; or a group —$A_k$—$R^7$, in which
A represents oxygen, sulfur, SO, $SO_2$, $C_1$–$C_6$-alkylene, $C_1$–$C_6$-alkyleneoxy, $C_1$–$C_6$-alkylenethio, $C_1$–$C_6$-oxyalkylene, $C_1$–$C_6$-oxyalkyleneoxy, $C_1$–$C_6$-alkyleneoxy-$C_1$–$C_6$-alkylene, $C_2$–$C_5$-alkenediyl or $C_2$–$C_5$-alkindiyl,
k represents a number 0 or 1 and
$R^7$ represents $C_1$–$C_{20}$-alkyl, $C_2$–$C_{20}$-alkenyl or $C_2$–$C_{20}$-alkinyl, each of which is optionally monosubstituted or polysubstituted by fluorine and/or chlorine, or represents $C_3$–$C_{12}$-cycloalkyl which is optionally monosubstituted to tri-substituted by identical or different substituents and in which one or two $CH_2$ groups which are not directly adjacent are optionally replaced by oxygen and/or sulfur, or phenyl which is optionally monosubstituted to pentasubstituted by identical or different substituents or pyridyl which is optionally monosubstituted to trisubstituted by identical or different substituents, cycloalkyl, phenyl or pyridyl substituents which may be mentioned in each case being:

halogen,
$C_1$–$C_{18}$-alkyl,
$C_1$–$C_8$-alkoxy-$C_1$–$C_8$-alkyl,
$C_1$–$C_8$-halogenoalkoxy,
$C_1$–$C_4$-halogenoalkyl,
$C_1$–$C_{18}$-alkoxy which is optionally interrupted by a further 1–3 oxygen atoms,
$C_1$–$C_{18}$-alkylthio,
$C_1$–$C_8$-halogenoalkylthio,
3,4-difluoromethylene dioxo,
3,4-tetrafluoroethylene dioxo,
benzyliminooxymethyl which is optionally substituted by $C_1$–$C_4$-alkyl, $C_3$–$C_6$-cycloalkyl and/or halogen,
cyclohexyl and cyclohexyloxy, each of which is optionally substituted by $C_1$–$C_6$-alkyl, $C_1$–$C_6$-alkoxy, cyclohexyl and/or phenyl;
alkoxy, pyridyloxy which is optionally monosubstituted or disubstituted by identical or different substituents from the series consisting of halogen, $C_1$–$C_4$-alkyl or $C_1$–$C_4$-halogenoalkyl;
phenyl, benzyl, phenoxy, phenylthio, benzyloxy and benzylthio, each of which is optionally monosubstituted or disubstituted by identical or different substituents from the series consisting of $C_1$–$C_{12}$-alkyl, halogen, $C_1$–$C_4$-halogenoalkyl, $C$–$C_6$-alkoxy, $C_1$–$C_6$-halogenoalkoxy, $C_1$–$C_6$-alkoxy-$C_1$–$C_6$-alkyl, $C_1$–$C_6$-alkoxyethyleneoxy, $C_1$–$C_6$-alkylthio or $C_1$–$C_6$-halogenoalkylthio; or $R^5$ preferably represents optionally substituted $C_3$–$C_{10}$-cycloalkyl in which one or two $CH_2$ groups which are not directly linked to each other are replaced by oxygen and/or sulfur, suitable substituents being the cycloalkyl substituents mentioned in the case of $R^7$.

$R^6$ preferably represents hydrogen, fluorine, chlorine, bromine, $C_1$–$C_8$-alkyl, $C_1$–$C_8$-halogenoalkyl, $C_1$–$C_8$-alkoxy or $C_1$–$C_8$-halogenoalkoxy.

m preferably represents a number 1, 2 or 3.
n preferably represents a number 1, 2 or 3.
X preferably represents O, S, $SO_2$, $CH_2$ or the group NH or N—$CH_3$.

Y preferably represents nitrogen or the group —CR$^9$
in which
R$^9$ represents hydrogen, fluorine, chlorine, bromine or C$_1$–C$_6$-alkyl.
R$^1$ particularly preferably represents fluorine, chlorine, bromine, C$_1$–C$_4$-alkyl or C$_1$–C$_4$-alkoxy.
R$^2$ particularly preferably represents hydrogen, fluorine, chlorine, bromine, C$_1$–C$_4$-halogenoalkyl or C$_1$–C$_4$-halogenoalkoxy.
R$^3$ particularly preferably represents hydrogen or methyl.
R$^4$ particularly preferably represents hydrogen or methyl.
R$^5$ particularly preferably represents fluorine, chlorine, bromine, trimethylsilylmethyl, trimethylsilylmethoxy, dimethylethylsilylmethyl, dimethylethylsilylmethoxy, butyldimethylsilylmethyl, butyldimethylsilylmethoxy
or a group —A$_k$—R$^7$
in which
A represents oxygen, sulfur, SO, SO$_2$ or C$_1$–C$_4$-alkylene, C$_1$–C$_4$-alkyleneoxy, C$_1$–C$_4$-alkylenethio, C$_1$–C$_4$-oxyalkylene, C$_1$–C$_4$-oxyalkyleneoxy, C$_1$–C$_4$-alkyleneoxy-C$_1$–C$_4$-alkylene, in particular
—CH$_2$—, —CH$_2$CH$_2$—, —CH(CH$_3$)—, —CH$_2$CH$_2$CH$_2$—, —CH(CH$_3$)CH$_2$—, —C(CH$_3$)$_2$—, —$_{CH2}$CH$_2$CH$_2$CH$_2$—, —CH(CH$_3$)CH$_2$CH$_2$—, —CH$_2$CH(CH$_3$)CH$_2$—, —CH$_2$O—, —CH$_2$CH$_2$O—, —CH(CH$_3$)—, —CH$_2$CH$_2$CH$_2$O—, —CH(CH$_3$)CH$_2$O—, —C(CH$_3$)O—, —CH$_2$CH$_2$CH$_2$CH$_2$O—, —CH(CH$_3$)CH$_2$CH$_2$O—, —CH$_2$CH(CH$_3$)CH$_2$O—, —OCH$_2$—, —CH$_2$S—, —OCH$_2$CH$_2$—, —OCH(CH$_3$)—, —OCH$_2$CH$_2$CH$_2$—, —OCH(CH$_3$)CH$_2$—, —OC(CH$_3$)$_2$—, —OCH$_2$CH$_2$CH$_2$CH$_2$—, —OCH(CH$_3$)CH$_2$CH$_2$ —, —OCH$_2$CH(CH$_3$)CH$_2$—, —CH$_2$OCH$_2$—, —CH$_2$SCH$_2$—, —CH$_2$OCH$_2$CH$_2$—, —OCH$_2$O—, —OCH$_2$CH$_2$O—, —OCH(CH$_3$)O—, —OCH$_2$CH$_2$CH$_2$O—, —OCH(CH$_3$)CH$_2$O—, —OC(CH$_3$)$_2$O—, —OCH$_2$CH$_2$CH$_2$O—, —OCH(CH$_3$)CH$_2$CH$_2$O— and —CH$_2$CH(CH$_3$)CH$_2$O— or C$_2$–C$_5$-alkenediyl or C$_2$–C$_5$-alkindiyl,
k represents a number 0 or 1 and
R$^7$ represents C$_1$–C$_{20}$-alkyl, C$_2$–C$_{20}$-alkenyl or C$_2$–C$_{20}$-alkinyl, each of which is optionally monosubstituted or polysubstituted by fluorine and/or chlorine, in particular ethyl, n-propyl, isopropyl, n-butyl, isobutyl, sec-butyl, tert-butyl, n-pentyl, isoamyl, neopentyl, n-hexyl, isohexyl, 3,3-dimethylbutyl, n-heptyl, 5-methylhexyl, 4-methylhexyl, 3-methylhexyl, 4,4-dimethylpentyl, n-octyl, 6-methylheptyl, n-nonyl, 7-methyloctyl, n-decyl, 8-methylnonyl, n-undecyl, 9-methyldecyl, n-dodecyl, 10-methylundecyl, n-undecyl, 9-methyldecyl, n-dodecyl, 10-methylundecyl, n-tridecyl, 11-methyldodecyl, n-tetradecyl, 12-methyltridecyl, n-pentadecyl, 13-methyltetradecyl, n-hexadecyl, n-heptadecyl, n-octadecyl, n-nonadecyl, n-eicosyl, vinyl, propenyl, isopropenyl, butenyl, pentenyl, hexenyl, heptenyl, octenyl, 3-methyl-1-butenyl, ethynyl, propynyl, butynyl, pentynyl, hexynyl, 3,3-dimethyl-1-butynyl, 4-methyl-1-pentynyl, 3-methyl-1-pentynyl, 5-methyl-1-hexynyl, 4-methyl-1-hexynyl, 3-methyl-1-hexynyl, octynyl, nonynyl, decynyl, undecynyl, dodecynyl, tridecynyl, tetradecynyl, pentadecynyl and hexadecynyl, each of which is optionally monosubstituted or polysubstituted by fluorine and/or chlorine; C$_3$–C$_{10}$-cycloalkyl which is optionally monosubstituted to trisubstituted by identical or different substituents, in particular cyclopropyl, cyclobutyl, cyclopentyl, cyclohexyl, cycloheptyl and cyclooctyl, phenyl which is optionally monosubstituted to pentasubstituted by identical or different substituents, or pyridyl which is optionally monosubstituted to trisubstituted by identical or different substituents; suitable cycloalkyl, phenyl and pyridyl substituents which may be mentioned in each case being:
F, Cl, Br,
C$_1$–C$_{18}$-alkyl,
C$_1$–C$_6$-alkoxy-C$_1$–C$_8$-alkyl,
C$_1$–C$_8$-alkoxy which is monosubstituted to hexasubstituted by identical or different substituents from the series consisting of F and Cl,
C$_1$–C$_2$-alkyl which is monosubstituted to pentasubstituted by identical or different substituents from the series consisting of F and Cl,
C$_1$–C$_{18}$-alkoxy,
(OCH$_2$H$_4$)$_{1-3}$—O—C$_1$–C$_6$-alkyl,
C$_1$–C$_{12}$-alkylthio,
C$_1$–C$_8$-alkylthio which is monosubstituted to hexasubstituted by identical or different substituents from the series consisting of F
and Cl,
3,4-difluoromethylenedioxo,
3,4-tetrafluoroethylenedioxo, the groups

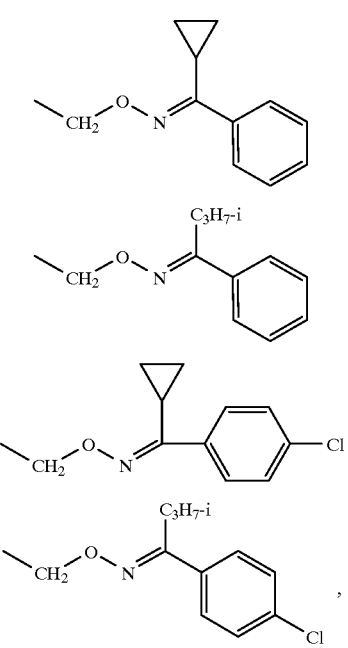

cyclohexyl and cyclohexyloxy, each of which is optionally substituted by C$_1$–C$_4$-alkyl, C$_1$–C$_4$-alkoxy, cyclohexyl or phenyl;
pyridyloxy which is optionally monosubstituted or disubstituted by identical or different substituents from the series consisting of F, Cl and CF$_3$,
phenyl, benzyl, phenoxy, phenylthio, benzyloxy and benzylthio, each of which is optionally monosubstituted or disubstituted by identical or different substituents from tiLe series consisting of
C$_1$–C$_{12}$-alkyl, F, Cl, Br, CF$_3$, C$_1$–C$_4$-alkoxy, C$_1$–C$_4$-alkoxy which is monosubstituted to hexasubstituted by identical or different substituents from the series consisting of F and Cl, $C_1$–$C_4$-alkoxy-$C_1$–$C_4$-alkyl, $C_1$–$C_4$-alkoxyethyleneoxy, $C_1$–$C_4$-alkylthio or $C_1$–$C_4$-alkylthio which is monosubstitutued to hexasubstituted by identical or different substituents from the series consisting of F and Cl, or $R^5$ particularly preferably represents optionally substituted $C_3$–$C_8$-cycloalkyl in which one or two $CH_2$ groups which are not linked to each other are replaced by oxygen and/or sulfur, suitable substituents being those mentioned in the case of $R^7$, $R^6$ particularly preferably represents hydrogen, fluorine, chlorine, bromine, $C_1$–$C_6$-alkyl, $C_1$–$C_6$-halogenoalkyl, $C_1$–$C_6$-alkoxy or $C_1$–$C_6$-halogenoalkoxy.

m particularly preferably represents a number 1, 2 or 3.

n particularly preferably represents a number 1 or 2.

X particularly preferably represents O, S, SO, $SO_2$, $CH_2$ or the group NH or N—$CH_3$.

Y particularly preferably represents a nitrogen atom or the group —$CR^9$ in which $R^9$ represents hydrogen, fluorine, chlorine, bromine or $C_1$–$C_6$-alkyl.

Very particularly preferred compounds of the formula (I-1)

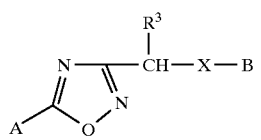

(I-1)

are those in which

A represents one of the radicals mentioned below

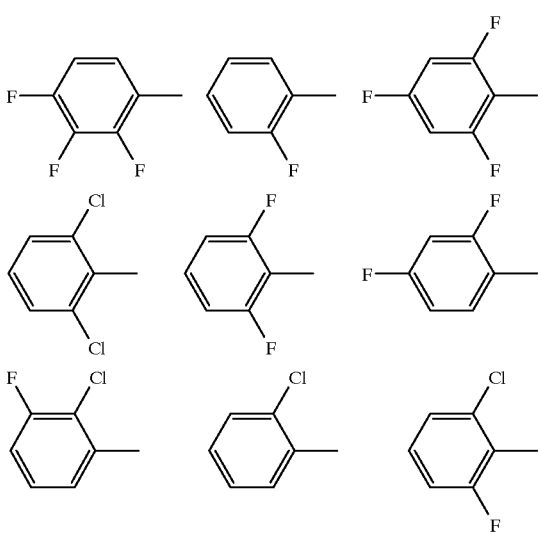

-continued

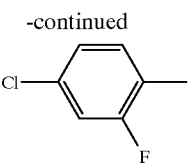

B represents one of the radicals

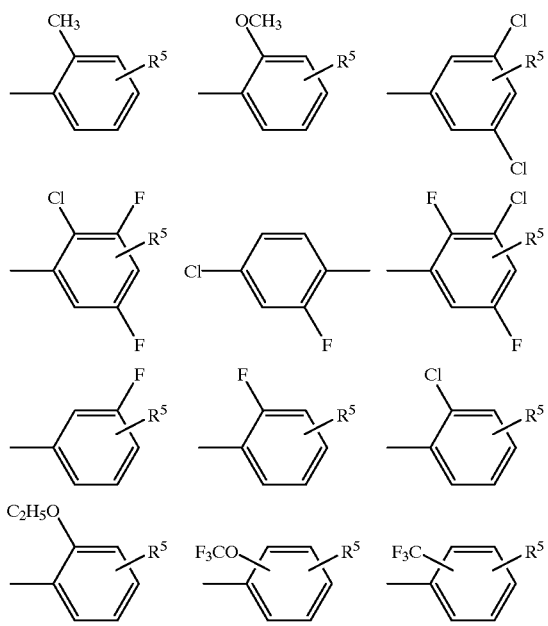

$R^3$ represents hydrogen or methyl,

X represents $CH_2$, O, S, SO or $SO_2$, and $R^5$ has the abovementioned meaning.

The compounds 5-(4-chlorophenyl)-3-[2-(2,4-dichlorophenyl)ethyl]-1,2,4-oxadiazole, (2,4-dichlorophenyl)-3-[2-(2,4-dichlorophenyl)ethyl]-1,2,4-oxadiazole and 3-(4-tert-butyl-phenoxymethyl)-5-(2,6-difluorophenyl)-1,2,4-oxadiazole are in each case excepted.

Unless otherwise specified, alkyl radicals, also in connection with hetero atoms such as, for example, in alkoxy or alkylthio, are in each case straight-chain or branched as far as this is possible. In the event that n=2, the radicals $R^6$ can be identical or different. In the event that m>1, the radicals $R^2$ can be identical or different.

The definitions of radicals can be combined as desired, that is to say combinations between the preferred and particularly preferred ranges are also possible. Preferred compounds of the formula (I) are those in which $R^1$, $R^2$, $R^3$, $R^4$, $R^5$, $R^6$, Y, m and n have the meanings given as being preferred.

Preferred compounds of the formula (I) are those in which $R^1$, $R^2$, $R^3$, $R^4$, $R^5$, $R^6$, Y, m and n have the meanings given as being particularly preferred.

Examples of compounds of the formula (I-1) according to the invention are listed in Tables 1–10.

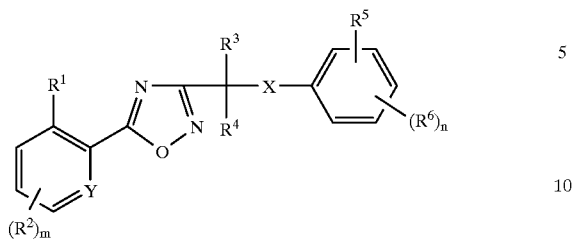
(I-1)
TABLE 1
| A | CH—R³ | X | ![aryl](aryl with R⁵, (R⁶)n) |
|---|---|---|---|
| 2,6-difluorophenyl | CH² | O | 4-t-C₄H₉-phenyl |
| 2,6-difluorophenyl | CH₂ | O | 4-n-C₆H₁₃-phenyl |
| 2,6-difluorophenyl | CH₂ | O | 4-n-C₁₂H₂₅-phenyl |
| 2,6-difluorophenyl | CH₂ | O | 4-(OCF₂—CHF₂)-phenyl |
| 2,6-difluorophenyl | CH₂ | O | 4-(OCH₂—CF₃)-phenyl |

TABLE 1-continued
| A | CH—R$_3$ | X | ![Ar](R$^5$, (R$^6$)$_n$) |
|---|---|---|---|
| 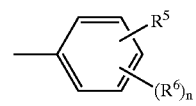 | CH$_2$ | O | 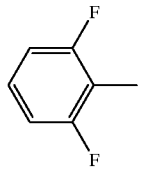 —OCF$_2$—CHFCH$_3$ |
| 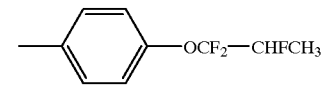 | CH$_2$ | O | 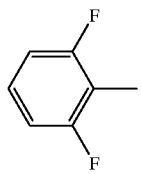 —CH$_2$CH$_2$—OC$_2$H$_5$ |
| 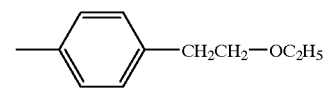 | CH$_2$ | O | 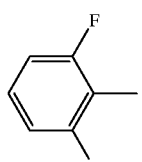 —CH$_2$CH$_2$—OC$_4$H$_9$ |
| 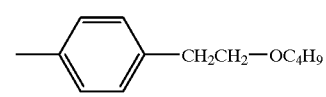 | CH$_2$ | O | 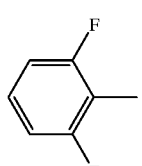 |
| 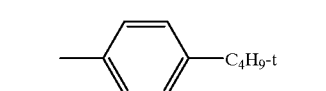 | CH$_2$ | O | 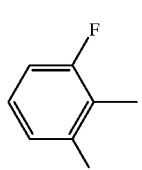 |
| 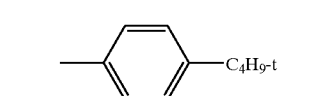 | CH$_2$ | O | 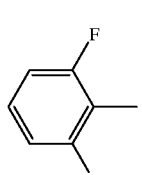 |
| 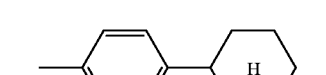 | CH$_2$ | O | 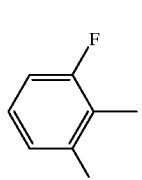 |

TABLE 1-continued
| A | CH—R₃ | X | ![aryl](R⁵, (R⁶)ₙ) |
|---|---|---|---|
| 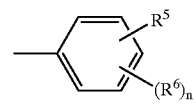 | CH₂ | O | 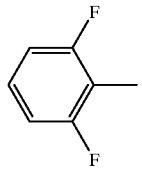 |
| 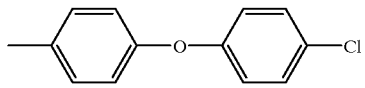 | CH₂ | O | 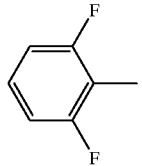 |
| 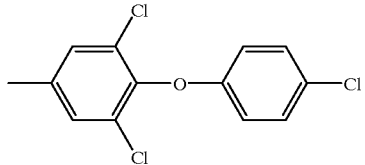 | CH₂ | O | 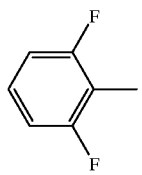 |
| 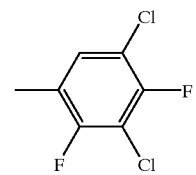 | CH₂ | O | 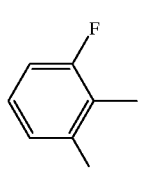 |
| 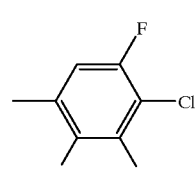 | CH₂ | O | 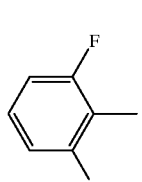 |
| 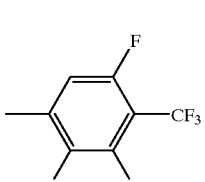 | CH₂ | O | 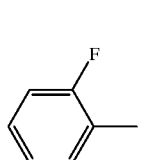 |
| 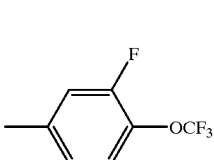 | CH₂ | O | 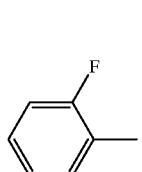—SC₄H₉-n |

TABLE 1-continued
| A | CH—R3 | X | 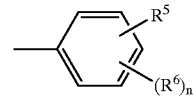 |
|---|---|---|---|
| 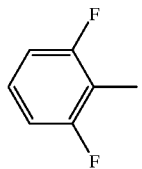 | CH² | O | 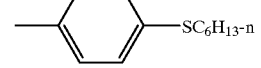 |
| 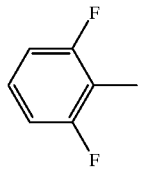 | CH₂ | O | 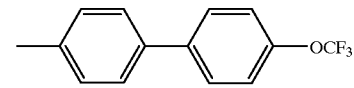 |
| 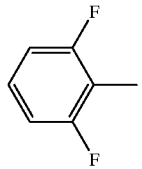 | CH₂ | O | 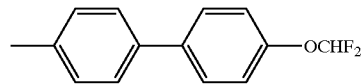 |
| 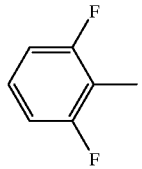 | CH₂ | O | 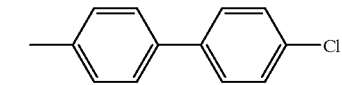 |
| 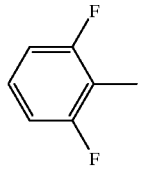 | CH₂ | O | 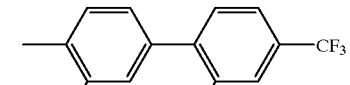 |
| 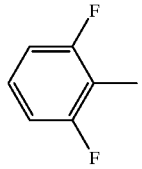 | CH₂ | O | 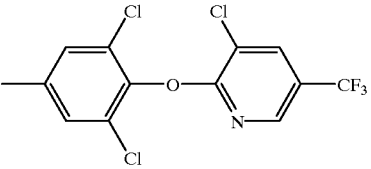 |
| 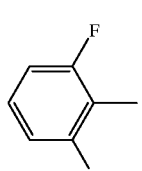 | CH₂ | O | 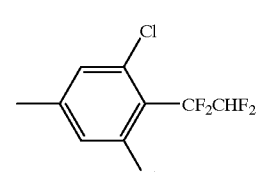 |

TABLE 1-continued

| A | CH—R³ | X | ![Ar with R⁵, (R⁶)ₙ] |
|---|---|---|---|
| 2,6-difluorophenyl | CH₂ | O | 4-(OCF₂—CHF—CF₃)phenyl |
| 2,6-difluorophenyl | CH₂ | O | 2,3-difluoro-4-CF₃-phenyl |
| 2,6-difluorophenyl | CH₂ | O | 3,5-difluoro-4-CF₃-phenyl |
| 2,6-difluorophenyl | CH₂ | O | 3-chloro-4-(2,6-dichloro-4-CF₃-phenoxy)phenyl |
| 2,6-difluorophenyl | CH₂ | O | 4-biphenyl |
| 2,6-difluorophenyl | CH₂ | O | 2,3,5-trichloro-4-OCF₃-phenyl |
| 2,6-difluorophenyl | CH₂ | O | 3-fluoro-4-(4-chlorophenoxy)phenyl |

TABLE 1-continued
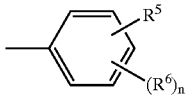
| A | CH—R³ | X | (aryl group with R⁵, R⁶) |
|---|---|---|---|
| 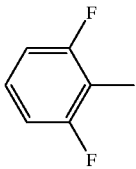 | CH² | O | 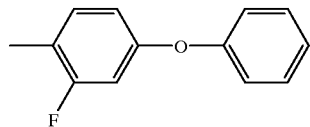 |
| 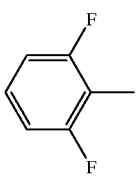 | CH₂ | O | 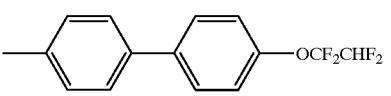 |
| 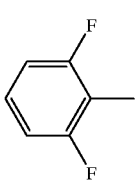 | CH₂ | O | 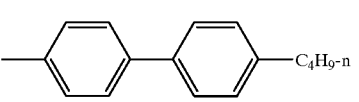 |
| 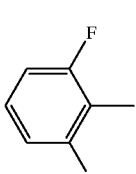 | CH₂ | O | 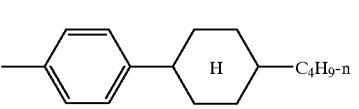 |
TABLE 2
Compounds of Table 1 in which
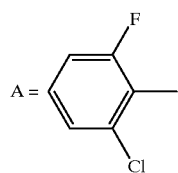
TABLE 3
Compounds of Table 1 in which
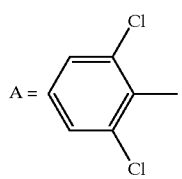
TABLE 4
Compounds of Table 1 in which
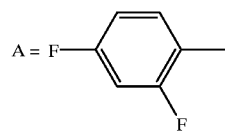
TABLE 5
Compounds of Table 1 in which
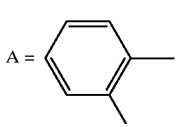

TABLE 6

Compounds of Table 1 in which

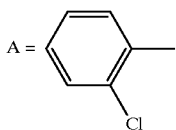

Table 7

Compounds of Tables 1–6 in which X=S;

Table 8

Compounds of Tables 1–6 in which X=CH$_2$;

Table 9

Compounds of Tables 1–6 in which X=NH;

Table 10

Compounds of Tables 1–9 in which —CH—R$^3$=—CH—CH$_3$.

If, for example, 3-chloro-2-methyl-phenoxy-acetamide oxime and 1,3-difluoro-2-(triethoxymethyl)-benzene are used for carrying out process a) according to the invention, the course of the reaction can be represented by the following equation:

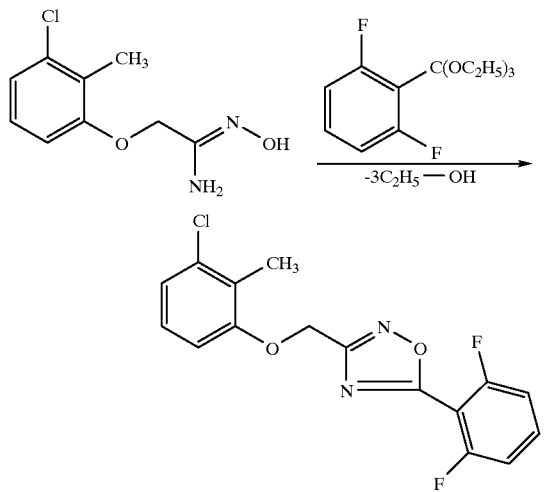

Formula (II) provides a general definition of the amide oximes required as starting substances for carrying out process a) according to the invention. In this formula, X, R$^3$, R$^4$, R$^5$, R$^6$ and n preferably represent those radicals which have already been mentioned in connection with the description of the substances of the formula (I) according to the invention as being preferred for these substituents.

The compounds of the formula (II), which are used as starting materials, are known in some cases (cf. for example Cervena' et al. Collect. Czech. Chem. Commun. 46 (1981) 5, pp. 1188–1198, EP 8 356, EP 7 529) or can be obtained by the processes described therein.

They are obtained, for example, when compounds of the formula (IX)

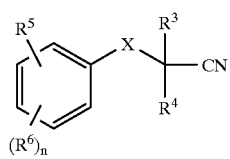

in which

R$^3$, R$^4$, R$^5$, R$^6$ and n have the abovementioned meanings, are reacted with hydroxyl amine or a salt thereof, such as, for example, hydroxylamine hydrochloride, at temperatures between 0° C. and 150° C., preferably between 20° C. and 100° C., if appropriate in the presence of a base such as, for example, sodium carbonate and in the presence of a diluent such as, for example, ethanol.

The compounds of the formula (IX) are known and/or can be prepared in a simple manner by customary processes. The compounds of the formula (IX) are obtained, for example, by reacting suitable phenols or anilines with a substituted acetonitrile, such as, for example, chloroacetonitrile, in the presence of a base such as sodium carbonate, sodium hydride or sodium hydroxide and in the presence of a diluent such as, for example, acetone (cf. the preparation examples).

Formula (III) provides a general definition of the orthocarboxylates furthermore to be used as starting substances for carrying out process a) according to the invention. Formulae (IV) and (V) provide general definitions of the carboxylic acid derivatives furthermore suitable for carrying out process a) according to the invention. In formulae (III) to (V), R$^1$, R$^2$, Y and m have the meanings which have already been mentioned in connection with the description of the substances of the formula (I) according to the invention as being preferred for this substituent. In formula (V), Z has the meaning of a suitable leaving group such as, for example, halogen or alkoxy. The orthocarboxylates of the formula (III) and the carboxylates of the formulae (IV) and (V) are generally known compounds of organic chemistry.

The compounds of the formulae (II) and (III) are preferably employed in the presence of an acidic catalyst. Suitable acidic catalysts are virtually all mineral acids or Lewis acids. The mineral acids preferably include hydrohalic acids, such as hydrofluoric acid, hydrochloric acid, hydrobromic acid or hydroiodic acid, and also sulfuric acid, phosphoric acid, phosphorous acid, nitric acid, and the Lewis acids preferably include aluminum(III) chloride, boron trifluoride or its etherate, titanium(IV) chloride and tin(IV) chloride.

The following Lewis acids are particularly preferably employed:

boron trifluoride or its etherate, aluminum(III) chloride.

When employing the compounds of the formula (III), process a) is generally carried out in such a manner that compounds of the formula (II) are combined with an excess of compounds of the formula (III) and the mixture is heated in the presence of an acidic catalyst. Compound (III) acts simultaneously as the diluent. The reaction time is approximately 1 to 4 hours. The reaction is carried out at temperatures between +20° C. and +200° C., preferably between +100° C. and +155° C. It is preferably carried out under the pressure which is established under the reaction conditions when the mixture is heated to the reaction temperature required.

The compounds of the formulae (II) are preferably reacted with the compounds of the formulae (IV) or (V) in the presence of a base. Suitable bases are all customary acid acceptors. The following can preferably be used:: tertiary amines, such as triethylamine, pyridine, diazabicyclooctane (DABCO), diazabicycloundecane (DBU), diazabicyclonones (DBN), Hunig base and N,N-dimethylaniline, furthermore alkaline earth metal oxides, such as magnesium oxide and calcium oxide, and moreover alkali metal carbonates and alkaline earth metal carbonates, such as sodium carbonate, potassium carbonate and calcium carbonate.

The reaction of the compounds of the formula (II) with the compounds of the formulae (IV) or (V) is generally carried out in the presence of a diluent.

Diluents which can be employed are all solvents which are inert to these compounds. The following can preferably be used: hydrocarbons, such as benzine, benzene, toluene, xylene and tetraline, furthermore halogenohydrocarbons, such as methylene chloride, chloroform, carbon tetrachloride, chlorobenzene and o-dichlorobenzene, moreover ketones, such as acetone and methyl isopropyl ketone, additionally ethers, such as diethyl ether, tetrahydrofuran and dioxane, in addition carboxylates, such as ethyl acetate, and also strongly polar solvents, such as dimethyl sulfoxide and sulfolane. If the acid halide is sufficiently stable to hydrolysis, the reaction can also be carried out in the presence of water.

When employing the compounds of the formula (IV) or (V), process a) is generally carried out in such a manner that compounds of the formula (II) are stirred with an equimolar amount or an excess of the compound of the formula (IV) or (V) at temperatures between −20° C. and 150° C., preferably between 0° C. and 100° C., in the presence of a diluent and in the presence of an at least equimolar amount of base until the reaction has ended.

When the reaction is complete, the reaction mixture is cooled and concentrated in vacuo, and the residue which remains is taken up in an organic solvent and processed in a manner known per se. The products obtained can be purified in the customary manner by recrystallization, distillation in vacuo or column chromatography (cf. also the preparation examples).

If, in process b), O-(2,6-difluorobenzoyl)-4-n-heptyl-phenoxy-acetamide oxime is employed as starting compound of the formula (VI), the process can be described by the following equation:

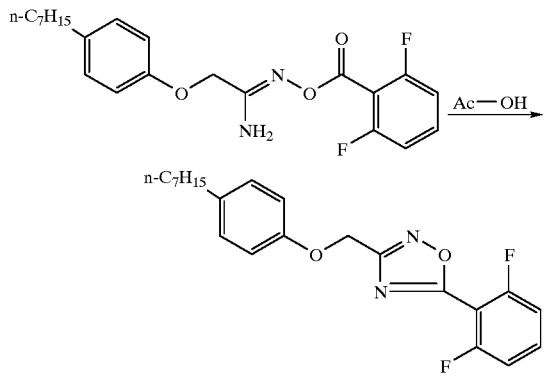

Preferred compounds of the formula (VI) which are employed in process b) are those in which X and the radicals $R^1$, $R^2$, $R^3$, $R^4$, $R^5$, $R^6$, n, m and Y have the meanings mentioned in the case of the compounds of the formula (I) as being preferred and particularly preferred.

The compounds of the formula (VI) are new and also are subject of the invention. They can originate in situ in process a) from compounds of the formula (II) and suitable carboxylic acid derivatives of the formulae (IV) and (V), but can also be employed in the isolated form, as is the case in process b).

Some of the compounds of the formula (VI) themselves have arthropodicidal or nematicidal properties.

The cyclization of the compounds of the formula (VI) is preferably carried out using diluents and, if appropriate, in the presence of a reaction auxiliary.

Diluents for carrying out process b) according to the invention are all inert organic solvents.

Examples which may be mentioned are: halogenohydrocarbons, in particular chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, dichlorobenzene, chlorotoluene, trichlorobenzene; alcohols such as methanol, ethanol, isopropanol, butanol; ethers, such as ethyl propyl ether, methyl-tert-butyl ether, n-butyl ether, di-n-butyl ether, di-isobutyl ether, di-iso-amyl ether, di-isopropyl ether, anisole, phenetol, cyclohexyl methyl ether, diethyl ether, ethylene glycol dimethyl ether, tetrahydrofuran, dioxane, dichlorodiethyl ether, nitrohydrocarbons, such as nitromethane, nitroethane, nitrobenzene, chloronitrobenzene, o-nitrotoluene; nitriles such as acetonitrile, butyronitrile, isobutyronitrile, benzonitrile, m-chlorobenzonitrile; aliphatic, cycloaliphatic or aromatic hydrocarbons such as heptane, hexane, nonane, cymene, benzine fractions within a boiling range of 70° C. to 190° C., cyclohexane, methylcyclohexane, petroleum ether, ligroin, octane, benzene, toluene, xylene; esters such as ethyl acetate, isobutyl acetate; amides, for example formamide, N-methyl ethyl ketone, carboxylic acids such as acetic acid, propionic acid, butyric acid. Mixtures of the abovementioned solvents and diluents are also suitable.

Carboxylic acids, such as acetic acid, or aromatic hydrocarbons, such as toluene and xylene, are preferred.

Substances which can be used as reaction auxiliaries are all suitable dehydrating agents such as, for example, dicyclohexylcarbodiimide [DCC] (cf., for example, F. Eloy Fortschr. chem. Forsch. 4 (1965) p. 807).

Process b) is generally carried out in such a manner that compounds of the formula (VI) are heated in a suitable diluent, if appropriate in the presence of a suitable reaction auxiliary. The reaction time is approximately 1 to 10 hours. The reaction is carried out at temperatures between +20° C. and +200° C., preferably between +70° C. and +170° C. The process is preferably carried out under the pressure which is established under the reaction conditions when the mixture is heated at the reaction temperature required.

When the reaction is complete, the reaction mixture is cooled, the entire reaction batch is concentrated, and the product is taken up in an organic solvent and processed in a manner known per se. The products obtained can be purified in the customary manner by recrystallization, distillation in vacuo or column chromatography (cf. also the preparation examples).

If, in process c) for the preparation of the new 1,2,4-oxadiazole derivatives of the formula (I), 3-chloromethyl-5-(2,6-difluoro-phenyl)-1,2,4-oxadiazole is employed as the compound of the formula (VII) and 4-(4-trifluoromethyl-phenoxy)-phenol as compound of the formula (VIII), the process can be represented by the following equation:

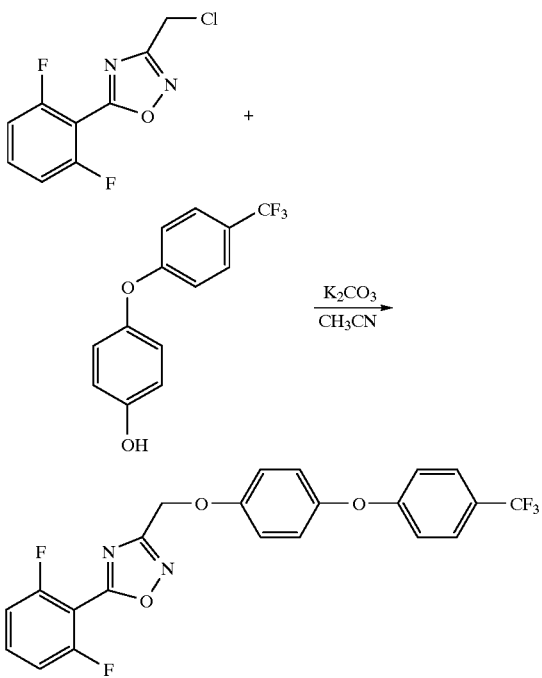

Formula (VII) provides a general definition of the 3,5-disubstituted 1,2,4-oxadiazoles required as starting substances for carrying out process c) according to the invention. In this formula, Y, $R^1$, $R^2$, $R^3$, $R^4$ and m preferably represent those radicals which have already been mentioned in connection with the description of the substances of the formula (I) according to the invention as being preferred for these substituents.

Z represents a suitable leaving group such as, for example, halogen, alkylsulfonyloxy or arylsulfonyloxy, such as chlorine, bromine, methanesulfonyloxy or toluenesulfonyloxy.

The compounds of the formula (VII) which are used as starting materials are known in some cases (cf., for example, German Offenlegungsschrift 2 406 786, GB 2 205 101; G. Palazzo J. Heterocyclic Chem. 16 (1979) p. 1469) or can be obtained by the processes described therein.

Some of the compounds of the formula (VII) themselves have arthropodicidal or nematicidal properties.

The reaction of the compounds of the formula (VII) with the compounds of the formula (VIII) is preferably carried out in the presence of diluents and in the presence of a basic reaction auxiliary.

Suitable diluents for carrying out process c) according to the invention are all inert organic solvents, as they have already been mentioned in the case of process b).

Substances which can be employed as basic reaction auxiliaries are all suitable acid-binding agents such as amines, in particular tertiary amines, and also alkali metal and alkaline earth metal compounds.

Examples which may be mentioned are the hydrides, hydroxides, oxides and carbonates of lithium, sodium, potassium, magnesium, calcium and barium, furthermore other basic compounds such as trimethylamine, tribenzylamine, triisopropylamine, tributylamine, tribenzylamine, tricyclohexylamine, triamylamine, trihexylamine, N,N-dimethyl-aniline, N,N-dimethyl-toluidine, N,N-dimethyl-p-aminopyridine, N-methyl-pyrrolidine, N-methylpiperidine, N-methyl-imidazole, N-methyl-pyrrole, N-methyl-morpholine, N-methyl-hexamethyleneimine, pyridine, quinoline, α-picoline, β-picoline, isoquinoline, pyrimidine, acridine, N,N,N',N'-tetra-methylenediamine, N,N,N'N'-tetra-ethylenediamine, quinoxaline, N-propyl-diisopropylamine, N,N'-dimethyl-cyclohexylamine, 2,6-lutidine, 2,4-lutidine, triethylenediamine, diazabicyclooctane (DABCO), diazabi-cyclonone (DBN) or diazabicycloundecene (DBU).

Tertiary amines such as, for example, triethylamine, N-methyl-morpholine or heteroaromatics or hydrides or hydroxides of potassium or sodium are preferably used.

Process c) is generally carried out in such a manner that compounds of the formula (VII) are combined with a small excess of compounds of the formula (VIII), if appropriate in the presence of a diluent, and the mixture is heated in the presence of a basic reaction auxiliary. The reaction time is approximately 5 to 30 hours. The reaction is carried out at temperatures between +20° C. and +200° C., preferably between +70° C. and +170° C. The process is preferably carried out under the pressure which is established under the reaction conditions when the mixture is heated at the reaction temperature required.

When the reaction is complete, the reaction mixture is cooled, the entire reaction batch is filtered, the filtrate is concentrated in vacuo, and the crude product which remains is worked up in a manner known per se. The products obtained can be purified in the customary manner by recrystallization, distillation in vacuo or, preferably, by column chromatography (cf. also the preparation examples).

In those compounds of the formula (I) which have been synthesized by processes a) to c) which have an arylthiomethyl radical, the group which has sulfur attached to it can be oxidized. The oxidation can be carried out by customary processes using suitable oxidants, such as peroxides (for example $H_2O_2$), permanganate, perbenzoic acid, or a mixture of potassium peroxomonosulfate, 2 $KHSO_5$, $KHSO_4$, and a solvent or solvent mixture (for example water, acetic acid, methanol) (cf. A. R. Katritzky, C. W. Rees in Comprehensive Heterocyclic Chemistry, Pergamon Press, Oxford, N.Y., 1984, Vol. 3, p. 96; D. J. Brown et al. Chem. Soc. (C), 1971, p. 256).

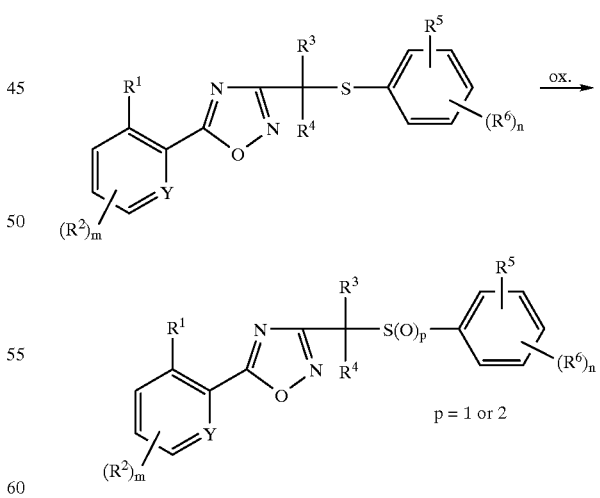

The oxidation can also be initiated or accelerated by means of catalysts.

The active compounds are suitable for combating animal pests, preferably arthropods and nematodes, and in particular insects and arachnids, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria app., *Bucculatrix thurberiella, Phyllocnistis citrella,* Agrotis spp., Euxoa spp., Feltia spp., *Earias insulana,* Heliothis app., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Bruchidius obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophiluis spp.,

*Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomoriuni pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia Spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp.

The plant-parasitic nematodes include Pratylenchus spp., *Radopholus similis, Ditylenchus dipsaci, Tylenchulus semipenetrans,* Heterodera spp., Meloidogyne spp., Apelenchoides spp., Longidorus spp., Xiphinema spp., Trichodorus spp.

The active compounds can be converted to the customary formulations, such as solutions, emulsions, suspensions, powders, dusts, pastes, soluble powders, granules, suspension-emulsion concentrates, natural and synthetic materials impregnated with active compound, and very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is liquid solvents and/or solid carriers, optionally with the use of surface-active agents, that is emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates as well as albumen hydrolysis products; as dispersing agents there are suitable: for example lignin-sulfite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospoholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The following compounds may be mentioned: Acrinathrin, alphamethrin, betacyfluthrin, bifenthrin, brofenprox, cis-resmethrin, clocythrin, cycloprothrin, cyfluthrin, cyhalothrin, cypermethrin, deltamethrin, esfenvalerate, etofenprox, fenpropathrin, fenvalerate, flucythrinate, fluvalinate, lambda-cyhalothrin, permethrin, pyresmethrin, pyrethrum, silafluofen, tralomethrin, zetamethrin.

Alanycarb, bendiocarb, benfuracarb, bufencarb, butocarboxim, carbaryl, cartap, ethiofencarb, fenobucarb, fenoxycarb, isoprocarb, methiocarb, methomyl, metolcarb, oxamyl, pirimicarb, promecarb, propoxur, terbam, thiodicarb, thiofanox, trimethacarb, XMC, xylylcarb, acephate, azinphos A, azinphos M, bromophos A, cadusafos, carbophenothion, chlorfenvinphos, chlormephos, chlorpyrifos, chloropyrifos M, cyanophos, demeton M, demeton-S-methyl, demeton S, diazinon, dichlorvos, dicliphos, dichlorfenthion, dicrotophos, dimethoate, dimethylvinphos, dioxathion, disulfoton, edifenphos, ethion, etrimphos, fenitrothion, fenthion, fonophos, formothion, heptenophos, iprobenfos, isazophos, isoxathion, phorate, malathion, mecarbam, mevinphos, mesulfenphos, methacrifos, methamidophos, naled, omethoate, oxydemeton M, oxydeprofos, parathion A, parathion M, phenthoate, phorate, phosalone, phosmet, phosphamidon, phoxim, pirimiphos A, pirimiphos M, propaphos, prothiophos, prothoate, pyraclophos, pyridaphenthion, quinalphos, salithion, sebufos, sulfotep, sulprofos, tetrachlorvinphos, temephos, thiomethon, thionazin, trichlorfon, triazophos, vamidothion, buprofezin, chlorfluazuron, diflubenzuron, flucycloxuron, flufenoxuron, hexaflumuron, pyriproxifen, tebufenozide, teflubenzuron, triflumuron, imidacloprid, nitenpyram, N-[(6-chloro-3-pyridinyl)-methyl]-N'-cyano-N-methyl-ethaneimideamide (NI-25), abamectin, amitrazin, avermectin, azadirachtin, bensultap, *Bacillus thuringiensis*, cyromazine, diafenthiuron, emamectin, ethofenprox, fenpyrad, fipronil, flufenprox, lufenuron, metaldehyd, milbemectin, pymetrozine, tebufenpyrad, triazuron, aldicarb, bendiocarb, benfuracarb, carbofuran, carbosulfan, chlorethoxyfos, cloethocarb, disulfoton, ethophrophos, etrimphos, fenamiphos, fipronil, fonofos, fosthiazate, furathiocarb, HCH, isazophos, isofenphos, methiocarb, monocrotophos, nitenpyram, oxamyl, phorate, phoxim, prothiofos, pyrachlofos, sebufos, silafluofen, tebupirimphos, tefluthrin, terbufos, thiodicarb, thiafenox, azocylotin, butylpyridaben, clofentezine, cyhexatin, diafenthiuron, diethion, emamectin, fenazacluin, fenbutatin oxide, fenothiocarb, fenpropathrin, fenpyrad, fenpyroximate, fluazinam, fluazuron, flucycloxuron, flufenoxuron, fluvalinate, fubfenprox, hexythiazox, ivemectin, methidathion, monocrotophos, moxidectin, naled, phosalone, profenofos, pyraclofos, pyridaben, pyrimidifen, tebufenpyrad, thuringiensin, triarathene and 4-bromo-2-(4-chlorophenyl)-1-(ethoxymethyl)-5-(trifluoromethyl)-1H-pyrrole-3-carbonitrile (AC 303630).

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use formed prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The active compounds according to the invention are not only active against plant, hygiene and stored product pests, but also, in the veterinary medicine sector, against animal parasites (ectoparasites and endoparasites) such as scaly ticks, Argasidae, scab mites, Trombidae, flies (stinging and sucking), parasitic fly larvae, lice, hair lice, bird lice, fleas and endoparasitic worms. For example, they have an outstanding activity against ticks, such as, for example, *Boophilus microplus*.

The active compounds of the formula (I) according to the invention are also suitable for combating arthropods which attack agricultural livestock such as, for example, cattle, sheep, goats, horses, pigs, donkeys, camels, buffalo, rabbits, chickens, turkeys, ducks, geese, honey bees, other domestic animals such as, for example, dogs, cats, cage birds, aquarium fish and so-called experimental animals such as, for example, hamsters, guinea pigs, rats and mice. By combating these arthropods, it is intended to reduce deaths and decreased performance (meat, milk, wool, hides, eggs, honey and the like), so that more economical and simpler animal keeping is made possible by using the active compounds according to the invention.

The application of the active compounds which can be used according to the invention occurs in the veterinary sector in a known fashion by enteral application in the form of, for example, tablets, capsules, potions, drenches, granules, pastes, boli, by the feed-through method, by means of suppositories, by means of parenteral application in the form, for example, of injections (intramuscular, subcutaneous, intravenous, interperitoneal and the like), implants, by nasal application, by dermal administration, for example in the form of dipping or bathing, spraying, pouring-on, spotting-on, washing, dusting, and with the aid of molded articles which contain active compound, such as collars, ear tags, tail cuffs, limb bands, halters, marking devices and the like.

The preparation and use of the substances according to the invention will be explained with reference to the examples below.

PREPARATION EXAMPLES

Example I-1

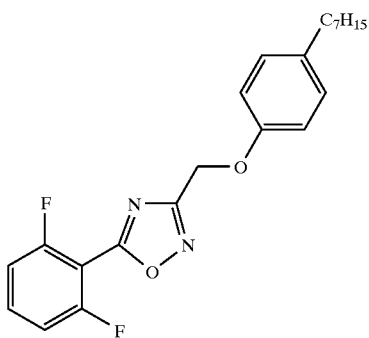

6.0 g (0.015 mol) of O-(2,6-difluoro-benzoyl)-4-n-heptyl-phenoxy-acetamide oxime are heated in 10 ml of glacial acetic acid until cyclization is complete (approximately 1 hour). The entire reaction mixture is then concentrated in vacuo, the product is taken up in ethyl acetate and washed with water, and the organic phase is dried over sodium sulfate. The solvent is subsequently distilled off in vacuo, and the crude product which remains is chromatographed over a silica gel column (silica gel Merck, particle size: 0.040 to 0.063 mm) using cyclohexane:ethyl acetate (6:1) as the eluent.

1.8 g (31.1% of theory) of 3-(4-n-heptyl-phenoxymethyl)-5-(2,6-difluorophenyl)-1,2,4-oxadiazole are obtained as an oil.

$^1$H NMR (400 MHz, CDCl$_3$, δ): 0.67–1.54 (3 m, 15H, —C$_7$H$_{15}$); 5.28 (s, 2H, —O—CH$_2$—); 6.96–7.59 (4 m, 7H, arom. H) ppm

Example I-2

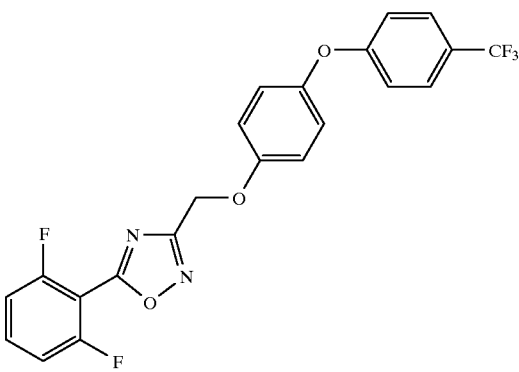

7.0 g (0.028 mol) of 4-(4-trifluoromethyl-phenoxy)-phenol are introduced into 100 ml of acetonitrile, 7.7 g (0.056 mol) of potassium carbonate and 6.5 g (0.028 mol) of 3-chloromethyl-5-(2,6-difluoro-phenyl)-1,2,4-oxadiazole are added, and the mixture is stirred for approximately 12 hours at reflux temperature. The potassium chloride which has precipitated is then removed, and the entire reaction batch is concentrated in vacuo. The crude product which remains can be recrystallized from isopropanol.

6.6 g (52.3% of theory) of 3-[4-(4-trifluoromethyl-phenoxy)-phenoxy-methyl]-5-(2,6-difluoro-phenyl)-1,2,4-oxadiazole of melting point 83–84° C. are obtained.

The compounds of the formula (I) which are listed in Table 11 below can be prepared analogously and following the general preparation instructions.

TABLE 11
Compounds of the formula (I)
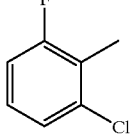
| Ex. No. | X | A | R³ | | Physical constants |
|---|---|---|---|---|---|
| I-3 | O | 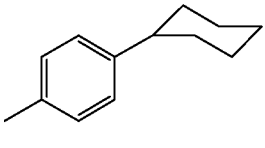 | H | 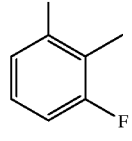 | m.p.: 46–48° C. |
| I-4 | O | 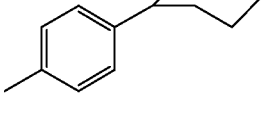 | H | 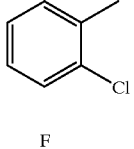 | m.p.: 46–47° C. |
| I-5 | O | 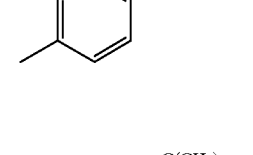 | H | 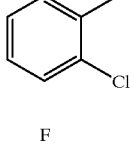 | m.p.: Oil |
| I-6 | O | 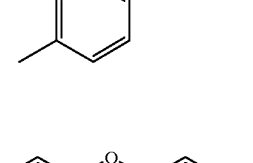 | H | 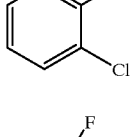 | m.p.: Oil |
| I-7 | O | 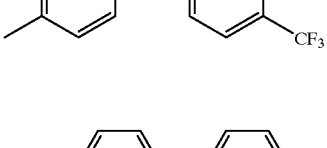 | H | 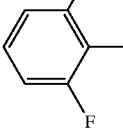 | m.p.: Oil |
| I-8 | O | 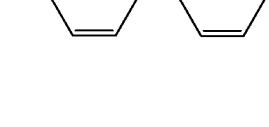 | H | 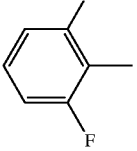 | m.p.: 122° C. |
| I-9 | O | 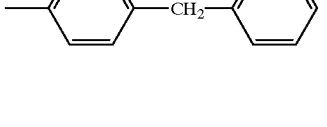 | H | | m.p.: 44–45° C. |

TABLE 11-continued

Compounds of the formula (I)

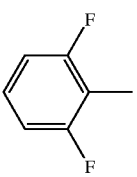

| Ex. No. | X | A | R³ | | Physical constants |
|---|---|---|---|---|---|
| I-10 | O | 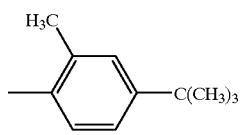 | H | 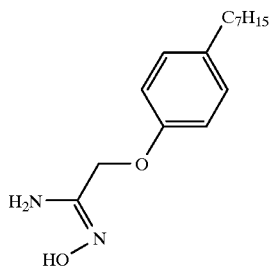 | Oil |

Preparation of the starting substances

Example (II-1)

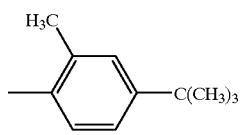

30.6 g (0.13 mol) of 4-n-heptyl-phenoxy-acetonitrile, 18.1 g (0.26 mol) of hydroxylamine hydrochloride and 27.6 g (0.26 mol) of sodium carbonate are stirred at reflux temperature in 100 ml of ethanol and 200 ml of water until the reaction is complete (approximately 24 hours). The entire reaction batch is subsequently introduced into water, and the mixture is extracted using methylene chloride. 34.3 g (99.8% of theory) of 4-n-heptyl-phenoxy-acetamide oxime are obtained.

$^1$H NMR (400 MHz, CDCl$_3$, δ): 0.67–1.53 (3 m, 15H, —C$_7$H$_{15}$); 4.54 (s, 2H, —O—CH$_2$—); 4.93 (br. s, 2H, —NH$_2$); 6.75–7.25 (4d, 4H, arom. H) ppm The compounds of the formula (II) listed in Table 12 below can be prepared analogously and following the general preparation instructions.

TABLE 12

Compounds of the formula (II)

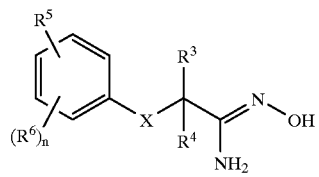
(II)

| Ex. No. | X | R³ | R⁴ | | Physical constants |
|---|---|---|---|---|---|
| II-2 | O | H | H | ![cyclohexyl-tolyl] | 4.36 (s, 2H, —O—CH²—)ᵃ⁾<br>5.57 (br. s, 2H, —NH₂) |
| II-3 | O | H | H | ![tolyl-O-phenyl-CF3] | 4.56 (s, 2H, —O—CH₂—)ᵇ⁾<br>4.98 (br. s, 2H, —NH₂) |
| II-4 | O | H | H | ![tert-butyl-tolyl] | 4.53 (s, 2H, —O—CH₂—)ᵃ⁾<br>4.96 (br. s, 2H, —NH₂) |

ᵃ⁾¹H NMR (400 MHz, CDCl₃, δ) in ppm;
ᵇ⁾¹H NMR (400 MHz, DMSO-d₆, δ) in ppm

Example (VI-1)

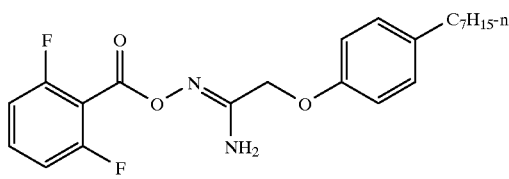

10.0 g (0.038 mol) of 4-n-heptyl-phenoxy-acetamide oxime and 10 ml of pyridine are introduced into 100 ml of chloroform, and 7.4 g (0.042 mol) of 2,6-difluorobenzoyl chloride are added dropwise at 0° C. to 5° C. After the mixture has been stirred for approximately twelve hours at room temperature, it is filtered, and the entire reaction batch is concentrated in vacuo. The reaction batch is subsequently treated with water, and the solid which separates out is filtered off with suction.

After recrystallization from diisopropyl ether, 7.0 g (46.9% of theory) of O-(2,6-difluorobenzoyl)-4-n-heptyl-phenoxy-acetamide oxime of melting point 99–100° C. are obtained.

The compounds of the formula (VI) listed in Table 13 below can be prepared analogously.

TABLE 13

Compounds of the formula (VI)

(IV)

[Structure: R⁵-substituted phenyl-(R⁶)ₙ—X—C(R³)(R⁴)—C(=N—O—C(=O)—aryl(R¹)(R²)ₘ with Y)—NH₂]

| Ex. No. | X | (R²)ₘ with R¹ and Y | R³ | R⁴ | (R⁵)/(R⁶)ₙ aryl | Physical constants |
|---|---|---|---|---|---|---|
| VI-2 | O | 2-F, 3-Cl phenyl | H | H | 4-(n-C₇H₁₅)phenyl | m.p.: 84–86° C. |
| VI-3 | O | 2,6-diF phenyl | H | H | 4-cyclohexylphenyl | m.p.: 140–141° C. |
| VI-4 | O | 2,6-diCl phenyl | H | H | 4-cyclohexylphenyl | m.p.: 139–140° C. |
| VI-5 | O | 2-F, 6-Cl phenyl | H | H | 4-cyclohexylphenyl | m.p.: — |
| VI-6 | O | 2,6-diF phenyl | H | H | 4-C(CH₃)₃ phenyl | m.p.: 89–90° C. |
| VI-7 | O | 2-F, 6-Cl phenyl | H | H | 4-C(CH₃)₃ phenyl | m.p.: 94–96° C. |

TABLE 13-continued

Compounds of the formula (VI)

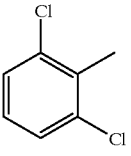

(IV)

| Ex. No. | X | (R²)ₘ | R³ | R⁴ | | Physical constants |
|---|---|---|---|---|---|---|
| VI-8 | O | 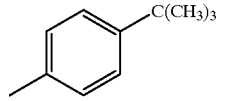 | H | H | 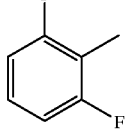 | m.p.: 143° C. |
| VI-9 | O | 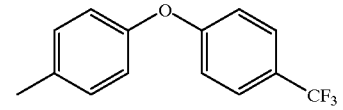 | H | H | 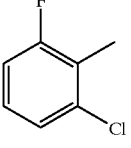 | m.p.: 122–124° C. |
| VI-10 | O | 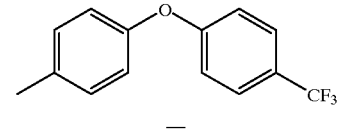 | —H | —H | 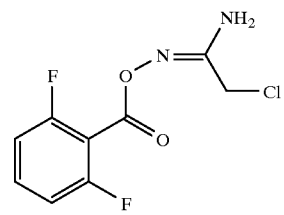 | m.p.: Oil |

Preparation of the precursors (VII)

Example (VII-1)

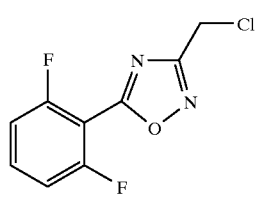

8.0 g (0.03 mol) of O-(2,6-difluoro-benzoyl-chloroacetamide oxime are heated in 16 ml of glacial acetic acid until cyclization is complete (approximately 2.5 hours). The entire reaction mixture is then concentrated in vacuo, the product is stirred with approximately 400 ml of water, and the mixture is subsequently extracted using methylene chloride. The organic phase is dried over sodium sulfate, and the solvent is distilled off in vacuo. The crude product which remains is chromatographed over a silica gel column (silica gel 60-Merck, particle size: 0.040 to 0.063 mm) using toluene:methanol (9:1) as the eluent. 3.4 g (49.1% of theory) of 3-chloromethyl-5-(2,6-difluoro-phenyl)-1,2,4-oxadiazole of melting point m.p.: 33–34° C. are obtained.

21.4 g (0.2 mol) of chloroacetamide oxime and 19.4 g (0.2 mol) of triethylamine are introduced into 100 ml of 1,4-dioxane, and 34.6 g (0.2 mol) of 2,6-difluoro-benzoyl chloride are added dropwise with cooling. After stirring has been continued at room temperature for approximately two hours, the entire reaction batch is poured into 400 ml of water, and the solid which separates out is filtered off with suction. After recrystallization from methanol, 15.3 g (32.4% of theory) of O-(2,6-difluoro-benzoyl)-chloroacetamide oxime of melting point 100–101° C. are obtained.

O-(2,6-Dichloro-benzoyl)-chloroacetamide oxime of melting point 133–134° C. is obtained analogously.

Example (IX-1)

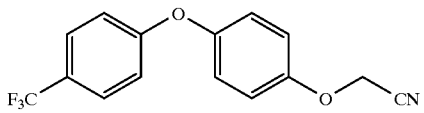

18.8 g (0.074 mol) of 4-(4-trifluoromethyl-phenoxy)-phenol and 10.2 g (0.074 mol) of potassium carbonate are introduced into 100 ml of acetone, 5.0 g (0.067 mol) of chloroacetonitrile are added in portions, and the mixture is stirred for 6 hours at reflux temperature. After cooling, the mixture is poured into water and extracted using ether. The organic phase is separated off, dried over magnesium sulfate and concentrated in vacuo.

18.8 g (86.6% of theory) of 4-(4-trifluoromethyl-phenoxy)-phenoxy-acetonitrile are obtained.

The compounds of the formula (IX) listed in Table 14 below can be prepared analogously.

Bean plants (*Phaseolus vulgaris*) which are severely infested with all stages of the greenhouse red spider mite (*Tetranychus urticae*) are sprayed with a preparation of active compound of the desired concentration.

After the specified periods of time, the activity in % is determined. 100% means that all the spider mites have been killed; 0% means that none of the spider mites have been killed.

In this test, a degree of destruction of at least 95% at an exemplary active compound concentration of 0.1% is shown after 7 days for example by the compounds of Preparation Examples I-1, I-2, I-4, I-5, I-7, I-8, I-9, I-10, (VI-6), (VI-7), (VI-9) and (VI-10).

Example B

Phaedon larvae test

Solvent: 7 parts by weight of dimethylformamide
Emulsifier: 1 part by weight of alkylaryl polyglycol ether To produce a suitable preparation of active compound, 1 part by weight of active compound is mixed with the stated

TABLE 14

Compounds of the formula (IX)

| Ex. No. | X | $R^2$ | $R^3$ | | Physical constants |
|---|---|---|---|---|---|
| IX-2 | O | H | H | 4-(2-methyl-2-propyl)phenyl (C(Me)$_3$) | 4.73 (s, 2H, —O—CH$_2$—)$^{a)}$ |
| IX-3 | O | H | H | 4-C$_7$H$_{15}$-phenyl | 4.73 (s, 2H, —O—CH$_2$—)$^{a)}$ |
| IX-4 | O | H | H | 4-cyclohexyl-phenyl | 4.71 (s, 2H, —O—CH$_2$—)$^{a)}$ |

$^{a)}$$^1$H NMR (400 MHz, CDCl$_3$, δ) in ppm

Example A

Tetranychus test (OP resistant/spray treatment)
Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with emulsifier-containing water to the desired concentrations.

amount of solvent and the stated amount of emulsifier, and the concentrate is diluted with emulsifier-containing water to the desired concentrations.

Cabbage leaves (*Brassica oleracea*) are treated by being dipped into the preparation of the active compound of the desired concentration and are infested with mustard beetle larvae (*Phaedon cochleariae*) while the leaves are still moist.

After the specified periods of time, the destruction in % is determined. 100% means that all the beetle larvae have been killed, 0% means that none of the beetle larvae have been killed.

In this test, a degree of destruction of 100% at an exemplary active compound concentration of 0.1% is shown after 7 days for example by the compound of Preparation Example I-6.

Example C

Panonychus test

Solvent: 3 parts by weight of dimethylfomamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with emulsifier-containing water to the desired concentrations.

Plum trees (*Prunus domestica*) approximately 30 cm high which are severely infested with all stages of the fruit tree red spider mite *Panonychus ulmi* are sprayed with a preparation of active compound of the desired concentration.

After the specified periods of time, the destruction in % is determined. 100% means that all the spider mites have been killed, 0% means that none of the spider mites have been killed.

In this test, a degree of destruction of at least 95% at an exemplary active compound concentration of 0.02% is shown after 7 days for example by the compounds of Preparation Examples I-1, I-2, I-4 and I-5.

Example D

Fly test (*Musca domestica*)

Test animals: *Musca domestica* adults, strain Reichswald (OP, SP, carbamate resistant)

Solvent: 35 parts by weight of ethylene glycol monomethyl ether 35 parts by weight of nonylphenol polyglycol ether.

To produce a suitable formulation, 3 parts by weight of active compound are diluted with 7 parts of the above-mentioned solvent/emulsifier mixture and the emulsion concentrate thus obtained is diluted with water to the particular desired concentration.

2 ml of this preparation of active compound are pipetted onto filter paper disks (φ9.5 cm) in Petri dishes of an appropriate size. After the filter paper has dried, 25 test animals are introduced into the Petri dishes and covered.

After 1, 3, 5 and 24 hours, the effectiveness of the preparation of active compound is determined. 100% means that all of the f lies have been killed, 0% means that no flies have been killed.

In this test, a degree of destruction of 100% at an exemplary active compound concentration of 1000 ppm is shown, for example, by the compound of Preparation Example (VII-1).

Example E

Plutella test

Solvent: 7 parts by weight of dimethylformamide

Emulsifier: 1 part by weight of alkylaryl polyglycol ether.

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the specified periods of time, the destruction in % is determined. 100% means that all the caterpillars have been killed; 0% means that none of the caterpillars have been killed.

In this test, a degree of destruction of 100% at an exemplary active compound concentration of 0.1% is shown after 7 days for example by the compound of Preparation Example I-3.

We claim:

1. A 1,2,4-oxadiazole derivative of the formula

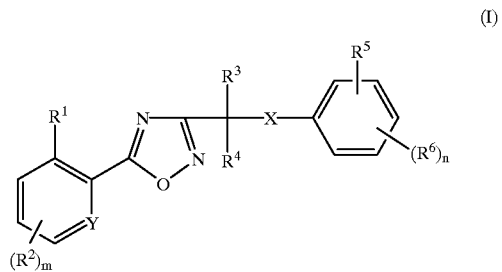

(I)

in which $R^1$ represents halogen, alkyl or alkoxy, $R^2$ represents hydrogen, halogen, halogenoalkyl or halogenoalkoxy, $R^3$ represents hydrogen or alkyl, $R^4$ represents hydrogen or alkyl, $R^5$ represents halogen, trialkylsilylalkyl, trialkylsilylalkoxy;

or a group —$A_k$—$R^7$ in which

A represents oxygen, sulfur, SO, $SO_2$, alkylene, alkyleneoxy, alkylenethio, oxyalkylene, oxyalkyleneoxy, alkyleneoxyalkylene, alkenediyl or alkindiyl, k represents a number 0 or 1, $R^7$ represents alkyl, halogenoalkyl, alkenyl, halogenoalkenyl, alkinyl, halogenoalkinyl, optionally substituted cycloalkyl, optionally substituted phenyl or optionally substituted pyridyl, or $R^5$ represents optionally substituted cycloalkyl, it being possible for one or two $CH_2$ groups which are not bonded directly to each other to be replaced by oxygen and/or sulfur, $R^6$ represents hydrogen, halogen, alkyl, halogenoalkyl, alkoxy or halogenoalkoxy, m represents a number 1, 2 or 3, n represents a number 1, 2 or 3, X represents O, S, SO, $SO_2$, $CH_2$ or a group N—$R^8$ in which $R^8$ represents hydrogen or alkyl and Y represents a nitrogen atom or the group C—$R^9$ in which $R^9$ represents hydrogen, halogen or alkyl;

with the exception of the compounds:

5-(4-chlorophenyl)-3-[2-(2,4-dichlorophenyl)ethyl]-1, 2,4-oxadiazole and 5-(2,4-dichlorophenyl)-3-[2-(2, 4-dichlorophenyl)ethyl]-1,2,4-oxadiazole and 3-(4- tert-butyl-phenoxymethyl)-5-(2,6-difluorophenyl)-1,2,4-oxadiazole.

2. A compound according to claim 1 of the formula (I-1)

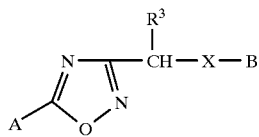

in which

A represents one of the radicals listed below

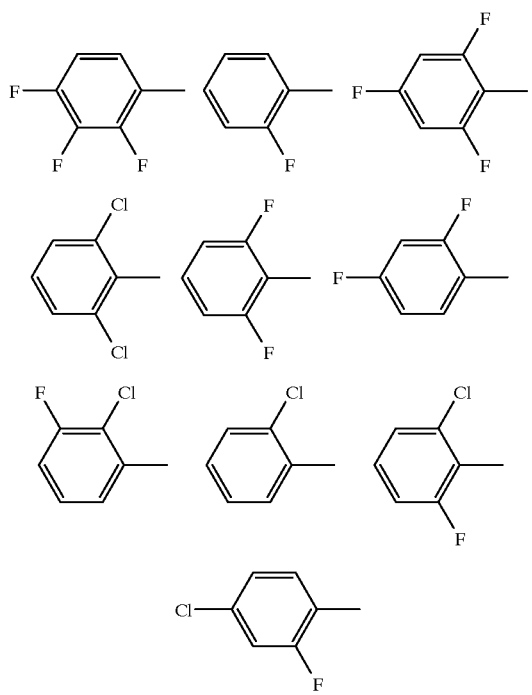

B represents one of the radicals

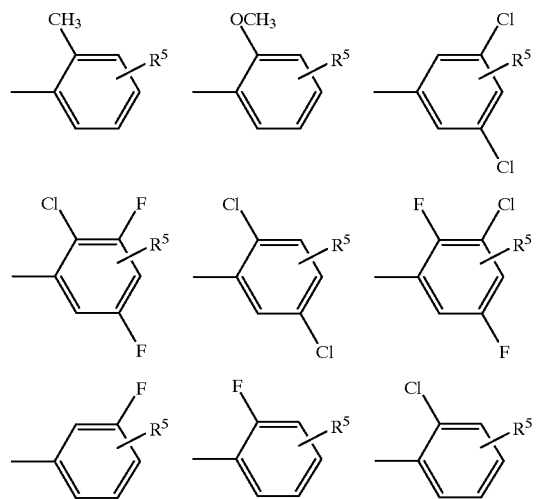

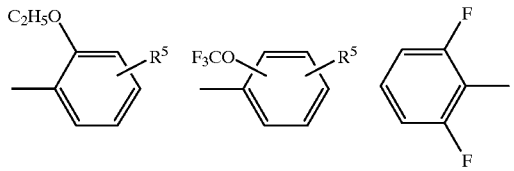

R³ represents hydrogen or methyl,
X represents $CH_2$, O, S, SO or $SO_2$ and
R⁵ has the meaning given in claim 1.

3. A 1,2,4-oxadiazole derivatives according to claim 1, in which

R¹ represents fluorine, chlorine, bromine, $C_1$–$C_6$-alkyl or $C_1$–$C_6$-alkoxy, R² represents hydrogen, fluorine, chlorine, bromine, $C_1$–$C_6$-halogenoalkyl or $C_1$–$C_6$-halogenoalkoxy, R³ represents hydrogen or $C_1$–$C_4$-alkyl, R⁴ represents hydrogen or $C_1$–$C_4$-alkyl, R⁵ represents fluorine, chlorine, bromine, tri-($C_1$–$C_8$-)-alkyl-silyl-($C_1$–$C_6$-)-alkyl or tri-($C_1$–$C_8$-)-alkyl-silyl-($C_1$–$C_6$-)-alkoxy, or a group —$A_k$—$R^7$,
in which
A represents oxygen, sulfur, SO, $SO_2$, $C_1$–$C_6$-alkylene, $C_1$–$C_6$-alkyleneoxy, $C_1$–$C_6$-alkylenethio, $C_1$–$C_6$-oxyalkylene, $C_1$–$C_6$-oxyalkyleneoxy, $C_1$–$C_6$-alkyleneoxy-$C_1$–$C_6$-alkylene, $C_2$–$C_5$-alkenediyl or $C_2$–$C_5$-alkindiyl, k represents a number 0 or 1 and R⁷ represents $C_1$–$C_{20}$-alkyl, $C_2$–$C_{20}$-alkenyl or $C_2$–$C_{20}$-alkinyl, each of which is optionally monosubstituted or polysubstituted by fluorine and/or chlorine, or represents $C_3$–$C_{12}$-cycloalkyl which is optionally monosubstituted to trisubstituted by identical or different substituents and in which one or two $CH_2$ groups which are not directly adjacent are optionally replaced by oxygen and/or sulfur, or phenyl which is optionally monosubstituted to pentasubstituted by identical or different substituents or pyridyl which is optionally monosubstituted to trisubstituted by identical or different substituents, wherein cycloalkyl, phenyl or pyridyl substituents are
halogen,
$C_1$–$C_{18}$-alkyl,
$C_1$–$C_8$-alkoxy-$C_1$–$C_8$-alkyl,
$C_1$–$C_8$-halogenoalkoxy,
$C_1$–$C_4$-halogenoalkyl,
$C_1$–$C_{18}$-alkoxy which is optionally interrupted by a further 1–3 oxygen atoms,
$C_1$–$C_{18}$-alkylthio,
$C_1$–$C_8$-halogenoalkylthio,
3,4-difluoromethylene dioxo,
3,4-tetrafluoroethylene dioxo,
benzyliminooxymethyl which is optionally substituted by $C_1$–$C_4$-alkyl, $C_3$–$C_6$-cycloalkyl and/or halogen,
cyclohexyl and cyclohexyloxy, each of which is optionally substituted by $C_1$–$C_6$-alkyl, $C_1$–$C_6$-alkoxy, cyclohexyl and/or phenyl;
pyridyloxy which is optionally monosubstituted or disubstituted by identical or different substituents selected from the group consisting of halogen, $C_1$–$C_4$-alkyl or $C_1$–$C_4$halogenoalkyl;

phenyl, benzyl, phenoxy, phenylthio, benzyloxy and benzylthio, each of which is optionally monosubstituted or disubstituted by identical or different substituents selected from the group consisting of $C_1$–$C_{12}$-alkyl, halogen, $C_1$–$C_4$-halogenoalkyl, $C_1$–$C_6$-alkoxy, $C_1$–$C_6$-halogenoalkoxy, $C_1$–$C_6$-alkoxy-$C_1$–$C_6$-alkyl, $C_1$–$C_6$-alkoxy-ethyleneoxy, $C_1$–$C_6$-alkylthio or $C_1$–$C_6$-halogenoalkylthio; or $R^5$ represents optionally substituted $C_3$–$C_{10}$-cycloalkyl in which one or two $CH_2$ groups which are not directly linked to each other are replaced by oxygen and/or sulfur, wherein the substituents are the cycloalkyl substituents mentioned in the case of $R^7$, $R^6$ represents hydrogen, fluorine, chlorine, bromine, $C_1$–$C_8$-alkyl, $C_1$–$C_8$-halogenoalkyl, $C_1$–$C_8$-alkoxy or $C_1$–$C_8$-halogenoalkoxy, m represents a number 1, 2 or 3, n represents a number 1, 2 or 3, X represents O, S, SO, $SO_2$, $CH_2$ or the group NH or N—$CH_3$, Y represents nitrogen or the group —$CR^9$ in which $R^9$ represents hydrogen, fluorine, chlorine, bromine or $C_1$–$C_6$-alkyl, with the exception of the compounds 5-(4-chlorophenyl)-3-[2-(2,4-dichlorophenyl)ethyl]-1,2,4-oxadiazole and 5-(2,4-dichlorophenyl)-3-[2-(2,4-dichlorophenyl)ethyl]-1,2,4-oxadiazole and 3-(4-tert-butyl-phenoxymethyl)-5-(2,6-difluorophenyl)-1,2,4-oxadiazole.

4. A 1,2,4-oxadiazole derivative according to claim 1, in which $R^1$ represents fluorine, chlorine, bromine, $C_1$–$C_4$-alkyl or $C_1$–$C_4$-alkoxy, $R^2$ represents hydrogen, fluorine, chlorine, bromine, $C_1$–$C_4$-halogenoalkyl or $C_1$–$C_4$-halogenoalkoxy, $R^3$ represents hydrogen or methyl, $R^4$ represents hydrogen or methyl, $R^5$ represents fluorine, chlorine, bromine, trimethylsilylmethyl, trimethylsilylmethoxy, dimethylethylsilylmethyl, dimethylethylsilylmethoxy, butyldimethylsilylmethyl, butyldimethylsilylmethoxy or a group —$A_k$—$R^7$ in which A represents oxygen, sulfur, SO, $SO_2$ or $C_1$–$C_4$-alkylene, $C_1$–$C_4$-alkyleneoxy, $C_1$–$C_4$-alkylenethio, $C_1$–$C_4$-oxyalkylene, $C_1$–$C_4$-oxyalkyleneoxy, $C_1$–$C_4$-alkyleneoxy-$C_1$–$C_4$-alkylene, in particular —$CH_2$—, —$CH_2CH_2$—, —$CH(CH_3)$—, —$CH_2CH_2CH_2$—, —$CH(CH_3)CH_2$—, —$C(CH_3)_2$—, —$CH_2CH_2CH_2CH_2$—, —$CH(CH_3)CH_2CH_2$—, —$CH_2CH(CH_3)CH_2$—, —$CH_2O$—, —$CH_2CH_2O$—, —$CH(CH_3)O$—, —$CH_2CH_2CH_2O$—, —$CH(CH_3)CH_2O$—, —$C(CH_3)_2O$—, —$CH_2CH_2CH_2CH_2O$—, —$CH(CH_3)CH_2CH_2O$—, —$CH_2CH(CH_3)CH_2O$—, —$OCH_2$—, —$CH_2S$—, —$OCH_2CH_2$—, —$OCH(CH_3)$—, —$OCH_2CH_2CH_2$—, —$OCH(CH_3)CH_2$—, —$OC(CH_3)_2$—, —$OCH_2CH_2CH_2CH_2$—, —$OCH(CH_3)CH_2CH_2$—, —$OCH_2CH(CH_3)CH_2$—, —$CH_2OCH_2$—, —$CH_2SCH_2$—, —$CH_2OCH_2CH_2$—, —$OCH_2O$—, —$OCH_2CH_2O$—, —$OCH(CH_3)O$—, —$OCH_2CH_2CH_2O$—, $OCH(CH_3)CH_2O$—, —$OC(CH_3)_2O$—, —$OCH_2CH_2CH_2CH_2O$—, —$OCH(CH_3)CH_2CH_2O$—, —$CH_2CH(CH_3)CH_2O$—, $C_2$–$C_5$-alkenediyl or $C_2$–$C_5$-alkindiyl, k represents a number 0 or 1, $R^7$ represents $C_2$–$C_{20}$-alkyl, $C_2$–$C_{20}$-alkenyl or $C_1$–$C_{20}$-alkinyl and each of which is optionally monosubstituted or polysubstituted by fluorine and/or chlorine, $C_3$–$C_{10}$-cycloalkyl which is optionally monosubstituted to trisubstituted by identical or different substituents, phenyl which is optionally monosubstituted to pentasubstituted by identical or different substituents or pyridyl which is optionally monosubstituted to trisubstituted by identical or different substituents, wherein cycloalkyl, phenyl and pyridyl substituents are F, Cl, Br, $C_1$–$C_{18}$-alkyl, $C_1$–$C_6$-alkoxy-$C_1$–$C_8$-alkyl, $C_1$–$C_8$-alkoxy which is monosubstituted to hexasubstituted by identical or different substituents selected from the group consisting of F and Cl, $C_1$–$C_2$-alkyl which is monosubstituted to pentasubstituted by identical or different substituents selected from the group consisting of F and Cl, $C_1$–$C_{18}$-alkoxy, $(OCH_2H_4)_{1-3}$—, O—$C_1$–$C_6$-alkyl, $C_1$–$C_{12}$-alkylthio, $C_1$–$C_8$-alkylthio which is monosubstituted to hexasubstituted by identical or different substituents selected from the group consisting of F and Cl, 3,4-difluoromethylenedioxo, 3,4-tetrafluoroethylenedioxo, the groups cyclohexyl, cyclohexyloxy, each of which is optionally substituted by $C_1$–$C_4$-alkyl, $C_1$–$C_4$-alkoxy, cyclohexyl or phenyl;

pyridyloxy which is optionally monosubstituted or disubstituted by identical or different substituents selected from the group consisting of F, Cl and $CF_3$, phenyl, benzyl, phenoxy, phenylthio, benzyloxy and benzylthio, each of which is optionally monosubstituted or disubstituted by identical or different substituents selected from the group consisting of $C_1$–$C_{12}$-alkyl, F, Cl, Br, $CF_3$, $C_1$–$C_4$-alkoxy, $C_1$–$C_4$-alkoxy which is monosubstituted to hexasubstituted by identical or different substituents selected from the group consisting of F and Cl, $C_1$–$C_4$-alkoxy-$C_1$–$C_4$-alkyl, $C_1$–$C_4$-alkoxy-ethyleneoxy, $C_1$–$C_4$-alkylthio or $C_1$–$C_4$-alkylthio which is monosubstituted to hexasubstituted by identical or different substituents selected from the group consisting of F and Cl, or $R^5$ represents optionally substituted $C_3$–$C_8$-cycloalkyl in which one or two $CH_2$ groups which are not linked to each other are replaced by oxygen and/or sulfur, wherein the substituents are those mentioned in the case of $R^7$, $R^6$ represents hydrogen, fluorine, chlorine, bromine, $C_1$–$C_6$-alkyl, $C_1$–$C_6$-halogenoalkyl, $C_1$–$C_6$-alkoxy or $C_1$–$C_6$-halogenoalkoxy, m represents a number 1, 2 or 3, n represents a number 1 or 2, X represents O, S, SO, $SO_2$, $CH_2$ or the group NH or N—$CH_3$, Y represents a nitrogen atom or the group —$CR^9$ in which $R^9$ represents hydrogen, fluorine, chlorine, bromine or $C_1$–$C_6$-alkyl, with the exception of the compounds:
5-(4-chlorophenyl)-3-[2-(2,4-dichlorophenyl)ethyl]-1,2,4-oxadiazole and 5-(2,4-dichlorophenyl)-3-[2-(2,4-dichlorophenyl)ethyl]-1,2,4-oxadiazole and 3-(4-tert-butyl-phenoxymethyl)-5-(2,6-difluorophenyl)-1,2,4-oxadiazole.

5. A 1,2,4-oxadiazole derivative according to claim 1, wherein X is O, SO, $SO_2$, $CH_2$, or a group N—$R^8$.

6. A 1,2,4-oxadiazole derivative according to claim 1, which has the formula

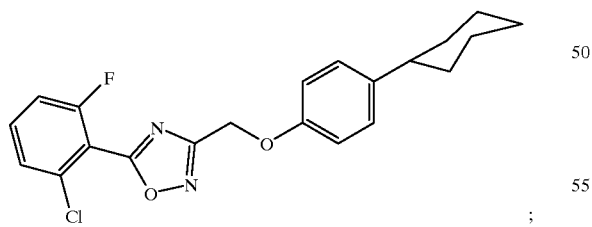

;

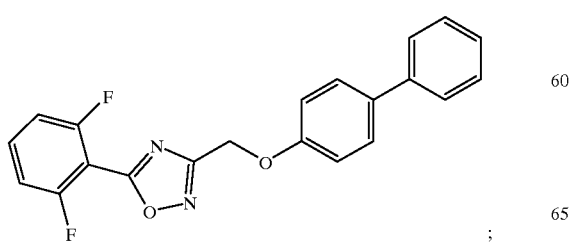

;

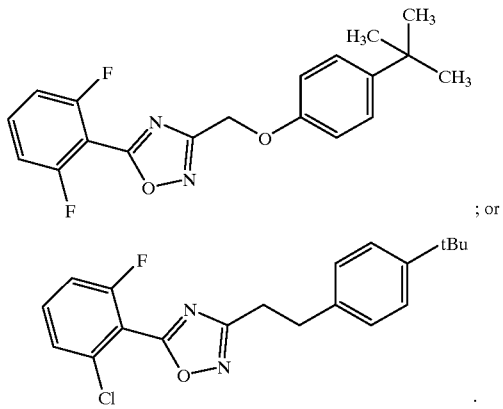

; or

7. A pesticidal composition which comprises an effective amount of a compound according to claim 1 and an inert carrier.

8. A method of combatting animal pests which comprises applying an effective amount of a compound according to claim 1 to said pests or to an environment where they reside.

9. A process for the preparation of 1,2,4-oxadiazole derivatives of the formula (I) as claimed in claim 1, wherein compounds of the formula (II)

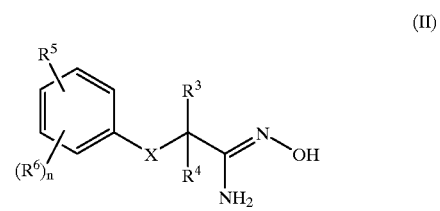

(II)

in which n, X, $R^3$, $R^4$, $R^5$ and $R^6$ have the meanings given in claim 1, are reacted with carboxylic acid derivatives of the formula (III), (IV) or (V)

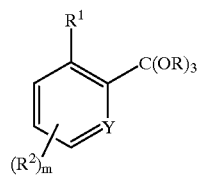

(III)

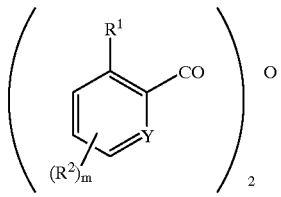

(IV)

-continued
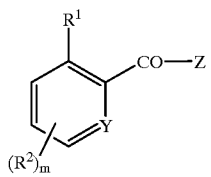
(V)
in which
R¹, R², m and Y have the meanings given in claim 1,
R represents alkyl and
Z represents a leaving group.
10. A process for the preparation of pesticides, which comprises mixing compounds of the formula (I) as claimed in claim 1 with extenders and/or surfactants.
\* \* \* \* \*